United States Patent [19]

Metzler et al.

[11] Patent Number: 5,578,742

[45] Date of Patent: Nov. 26, 1996

[54] BIS-PHENYL-HEXENES

[76] Inventors: Manfred Metzler, Theodor-Heuss-Strasse 3, D-67663 Kaiserslautern; Reinhard Pechan, Elektrastrasse 14, D-81925 München, both of Germany

[21] Appl. No.: 318,675

[22] PCT Filed: Apr. 13, 1993

[86] PCT No.: PCT/EP93/00892

§ 371 Date: Oct. 14, 1994

§ 102(e) Date: Oct. 14, 1994

[87] PCT Pub. No.: WO93/22262

PCT Pub. Date: Nov. 11, 1993

[30] Foreign Application Priority Data

Apr. 15, 1992 [DE] Germany .................. 42 12 628.2

[51] Int. Cl.$^6$ .................................................. C07C 15/18
[52] U.S. Cl. ........................................................... 585/436
[58] Field of Search ............................. 585/436; 514/765

[56] References Cited

PUBLICATIONS

Chemical Abstract CA 77:14579 (1972).
Chemical Abstract CA 99:70314 (published 1983).
Chemical Abstracts, vol. 77, No. 3, 17 Jul. 1972, Abstract No. 14579x.
Owen et al., "Papillomatous Growths 'on Internal Genitalia of Bitches Administered the Synthetic Estrogen Tran-4, 4'-Dimethyl-α,α$^1$-Diethylstilbene", *Technology and Applied Pharmacology*, 21, 582–585 (1972).

*Primary Examiner*—Asok Pal
*Attorney, Agent, or Firm*—Nikaido, Marmelstein, Murray & Oram LLP

[57] ABSTRACT

The present invention concerns new substituted 3,4-bis(phenyl)-3-hexenes and pharmaceutical compositions which contain these compounds as active substances.

7 Claims, No Drawings

BIS-PHENYL-HEXENES

BACKGROUND OF THE INVENTION

The present invention concerns new chemical compounds from the group of bis-phenyl-hex-3-enes, a process for their production and their use as therapeutic agents.

Numerous diseases in humans are due to an uncontrolled growth of body cells. This disturbance in proliferation can lead to a benign degeneration e.g. psoriasis vulgaris in the case of keratinocytes or β-thalassaemia in the case of erythrocytes or it can also lead to a malignant degeneration such as in all forms of cancer.

The aim of a cancer therapy is to completely destroy or at least to significantly inhibit the growth of the tumour cells. In addition to surgical measures and radiation therapy, chemotherapeutic agents such as 5-fluorouracil, cytosine-arabinoside etc. are also available nowadays for the treatment of cancer patients. A disadvantage in the use of these chematherapeutic agents is, however, that in addition to the tumour cells they also can damage healthy regions of the organism. Therefore a search has been going on for several years for less aggressive methods of treatment. Thus the use of tamoxifen for mammacarcinomas brought the first very promising results (Jordan, Antiestrogens in Cancer Treatment, in: Stoll, B. A., Endocrine Management of Cancer, Karger, Basel (1988), 57–65). However, numerous cancer diseases (e.g. colonic and pancreatic carcinoma) cannot yet be treated to an adequate extent by drugs (Cohen et al., Colorectal Cancer, and Brennan et al., Cancer of the Pancreas in: DeVita, V. T., Helman, S. and Rosenberg, St. A., Cancer, Lippincott Co., 3rd Edition (1989)).

One of the main causes for carcinogenesis is considered to be mistakes in the expression of so-called oncogenes such as myc or ras (Tabin et al., Nature, 300 (1982), 143–149). An important regulation mechanism of gene expression—also in oncogenes—is the degree of methylation of DNA (Doerfler, J. gen. Virol., 57 (1981) 1–20). Thus using ras and myc oncogenes as an example it was possible to detect a hypomethylation in the expressed cancerogenic status (Feinberg et al., Biophys. Res. Comm., 111 (1983) 47–54; Cheah et al., J. Nat. Cancer Inst., 73, (1984), 1057–1061)). Furthermore it is known that the growth as well as the correct somatic function of degenerate cells can be regulated by a targetted control of DNA methylation. This was shown by Ley et al. (DNA methylation and globin gene expression in patients treated with 4-azacytidine, in: Globin Gene Expression and Hematopoietic Differentiation, Alan P. Liss, N.Y. (1983), 457–474). A further direct correlation between the methylation of DNA and disturbances in the central nervous system were found in HIV-positive patients (Keating et al., Lancet, 337 (1991) 935–939).

Moreover it was possible in in vitro cell culture experiments to establish a direct correlation between malignant transformation and DNA hypomethylation on the one hand and between concentration-dependent growth inhibition of tumour cells (from humans and animals) and DNA hypermethylation on the other hand (Pechan, (1987), Dissertation, University Würzburg).

SUMMARY OF THE INVENTION

An object of the present invention was to provide new compounds which exhibit a pharmaceutical efficacy in the treatment of diseases that are associated with degenerate cell growth i.e. disturbances of cell proliferation.

The object according to the invention is achieved by a 3,4-bis(4-X-phenyl)-3-hexene in which the groups X in each case represent alkyl, alkenyl or alkinyl residues with 1 to 10 carbon atoms which are substituted if desired, or aralkyl residues with 1 to 10 non-aromatic carbon atoms which are substituted if desired.

DESCRIPTION OF THE PREFERRED EMBODIMENTS

The groups X are preferably alkyl, alkenyl or alkinyl residues each with 1 to 5 carbon atoms which are substituted if desired.

The groups X in the compounds according to the invention are particularly preferably alkyl residues with 2 to 4 carbon atoms, the groups X are most preferably ethyl, n-propyl, isopropyl, sec.-butyl or tert. butyl residues.

The term "alkyl residue" according to the invention encompasses aliphatic or cycloaliphatic hydrocarbon residues which, however, can also optionally have one or several inert substituents (e.g. halogen groups or alkoxy groups).

An "alkenyl residue" according to the present invention is an optionally (inertly) substituted hydrocarbon residue with one or several C=C bonds e.g. a vinyl or an allyl residue. An analogous definition applies to the term "alkinyl residue". The term "aralkyl residue" denotes an alkyl, alkenyl or alkinyl residue which additionally carries an aryl group that is substituted if desired, e.g. a benzyl residue.

The compounds according to the invention can be obtained by a method which is characterized in that a 1-(4-X-phenyl)-1-propanone (in which X is in accordance with the above definition) is reacted in the presence of a transition metal chloride, zinc dust and a base in an inert solvent and the desired compound is isolated from the reaction mixture by purification.

The transition metal chloride is preferably titanium tetrachloride and the base is preferably pyridine. The inert solvent is preferably 1,4-dioxane and the reaction is preferably carried out at the reflux temperature of the solvent.

Further details of this method are described in a publication by McMurry (J. Org. Chem. 54 (1989), 3748–3749).

Surprisingly the substances according to the invention significantly inhibit the growth of tumour cells in vitro. Thus it is to be expected that the compounds would be suitable as therapeutic agents for the treatment of diseases which are associated with degenerate cell growth.

The present invention therefore also concerns a pharmaceutical composition which contains one or several of the compounds according to the invention as the active substance and if desired, common pharmaceutical carrier substances, fillers, diluents or/and auxiliary substances.

The compounds according to the invention are suitable for all indication ranges in human and veterinary medicine in which the growth of degenerate body cells can be inhibited or/and influenced by DNA hypermethylation. In this connection cancer, psoriasis or AIDS are worthy of particular mention.

The pharmaceutical composition according to the invention can in this case be administered in any desired formulations which contain the compounds according to the invention. Examples of suitable formulations are for instance tablets, capsules, granulates, solutions, ointments or aerosols. The production of such formulations is sufficiently well-known to a person skilled in the area of pharmacy so that an extensive description would not appear to be necessary.

The following examples serve to further elucidate the invention.

EXAMPLE 1

Synthesis of 3,4-bis(4-alkylphenyl)-3-hexenes according to McMurry (1989, supra)

108 mmol titanium tetrachloride is added dropwise while stirring (ice cooling, argon atmosphere) to 200 ml 1,4-dioxane. 200 mmol zinc dust and 8 ml pyridine are added in small portions to this solution. After the slow (30 minutes) addition of 1-(4-alkylphenyl)-1-propanone the reaction solution is heated under reflux (20 hours). After cooling, this solution is admixed with 200 ml 10% potassium carbonate solution. The suspension formed in this manner is extracted by shaking with 50 ml diethyl ether, washed with water and dried over magnesium sulfate.

For purification the crude product is filtered over silica gel using petroleum ether/diethyl ether (4/1) and subsequently separated by column chromatography (silica gel, petroleum ether/diethyl ether 2/1). The pure substance (colourless) crystallizes in the cold after several days.

The following substances were prepared:

| | | |
|---|---|---|
| 3,4-Bis(4-ethylphenyl)-3-hexene | yield: | 33% |
| | melting point: | 34.6° C. |
| 3,4-Bis(4-n-propylphenyl)-3-hexene | yield: | 14% |
| | boiling point: | 84° C./0.04 torr (impure) |
| 3,4-Bis(4-i-propylphenyl)-3-hexene | yield: | 16% |
| | melting point: | 39.5° C. |
| 3,4-Bis(4-s-butylphenyl)-3-hexene | yield: | 19% |
| | boiling point: | 87° C./0.03 torr |
| 3,4-Bis(4-t-butylphenyl)-3-hexene | yield: | 10% |
| | melting point: | 84.6° C. |

EXAMPLE 2

Growth inhibition of tumour cells in vitro $10^4$ to $10^5$ tumour cells were sown in each case in 3 ml IBR medium (15% foetal calf serum, 25 U/ml penicillin-streptomycin) in cell culture flasks (T25, Greiner). After a growth phase of 4 hours (37° C., 12% $CO_2$) 50 μM of each test substance dissolved in 0.1% DMSO and 0.1% DMSO (control) were added. 3,4-Bis(4-ethylphenyl)-3-hexene, 3,4-bis(4-i-propylphenyl)-3-hexene and 3,4-bis(4-t-butylphenyl)-3-hexene were used as the test substances.

Cell counting (Neubauer counting chamber) was carried out at intervals of 24 hours over a period of 5 days. After 3 days the medium was exchanged and the test substances (see example 1) were again added at the same concentration.

The growth of HT29 liver carcinoma cells (human) could be inhibited by about 40% and that of in vitro transformed hamster cells by about 30%.

We claim:

1. A 3,4-bis (4-X-phenyl)-3-hexene in which the groups X in each case represent alkyl residues with 2 to 4 carbon atoms, substituted or unsubstituted alkenyl or alkynyl residues with 2 to 10 carbon atoms, or substituted or unsubstituted aralkyl residues with 1 to 10 non-aromatic carbon atoms.

2. Compound as claimed in claim 1, wherein the groups X in each case represent substituted or unsubstituted alkenyl or alkynyl residues with 2 to 5 carbon atoms.

3. Compounds as claimed in claim 1, wherein the groups X are ethyl, n-propyl, iso-propyl, sec.-butyl or tert.-butyl residues.

4. Process for the production of a compound as claimed in claim 1, wherein a 1-(4-X-phenyl)-1-propanone in which X is defined as in claim 1, is reacted in the presence of a transition metal chloride, zinc dust and a base in an inert solvent and the desired compound is isolated from the reaction mixture by purification.

5. Pharmaceutical composition, wherein it contains one or several compounds as claimed in claim 1 as the active substance and if desired, conventional pharmaceutical carrier substances, fillers, diluents or/and auxiliary substances.

6. A method of treating a disease which is associated with degenerate cell growth in a patient in need of such treatment, comprising administering to the patient a disease-treating effective amount of the compound as claimed in claim 1.

7. The method as claimed in claim 6, wherein the disease is selected from the group consisting of cancer, psoriasis and AIDS.

* * * * *